United States Patent
Mittal et al.

(10) Patent No.: US 9,085,556 B2
(45) Date of Patent: Jul. 21, 2015

(54) SALTS OF DEXLANSOPRAZOLE AND THEIR PREPARATION

(75) Inventors: Anu Mittal, Kurukshetra (IN); Anmol Kumar Ray, Jaipur (IN); Mahavir Singh Khanna, New Delhi (IN); Rajesh Kumar Thaper, Jammu (IN); Mohan Prasad, Gurgaon (IN)

(73) Assignee: RANBAXY LABORAOTORIES LIMITED, New Delhi (IN)

(*) Notice: Subject to any disclaimer, the term of this patent is extended or adjusted under 35 U.S.C. 154(b) by 64 days.

(21) Appl. No.: 13/638,310

(22) PCT Filed: Mar. 29, 2011

(86) PCT No.: PCT/IB2011/051342
§ 371 (c)(1),
(2), (4) Date: Feb. 11, 2013

(87) PCT Pub. No.: WO2011/121546
PCT Pub. Date: Oct. 6, 2011

(65) Prior Publication Data
US 2013/0197233 A1    Aug. 1, 2013

(30) Foreign Application Priority Data
Mar. 31, 2010  (IN) .............................. 795/DEL/2010

(51) Int. Cl.
*C07D 401/12* (2006.01)

(52) U.S. Cl.
CPC ................................... *C07D 401/12* (2013.01)

(58) Field of Classification Search
CPC ..................................................... C07D 401/12
USPC ........................................................ 546/273.7
See application file for complete search history.

(56) References Cited

U.S. PATENT DOCUMENTS

| | | | |
|---|---|---|---|
| 6,462,058 B1 | 10/2002 | Fujishima et al. | 514/338 |
| 7,271,182 B2 | 9/2007 | Kamiyama et al. | 514/338 |
| 7,285,668 B2 | 10/2007 | Hashimoto et al. | 546/273.7 |
| 2007/0004779 A1 | 1/2007 | Hashimoto et al. | 514/338 |
| 2011/0028518 A1* | 2/2011 | Kolla et al. | 514/338 |

FOREIGN PATENT DOCUMENTS

| | | | | |
|---|---|---|---|---|
| EP | 0 268 956 | 11/1987 | ........... | C07D 401/12 |
| EP | 1 552 833 | 7/2005 | ......... | A61K 31/4439 |
| EP | 1 607 395 | 12/2005 | ........... | C07D 401/12 |
| WO | WO 2009/117489 | 9/2009 | ........... | C07D 403/12 |

* cited by examiner

*Primary Examiner* — Patricia L Morris

(57) ABSTRACT

The present invention relates to the salts of dexlansoprazole in amorphous form. The present invention further relates to processes for the preparation of salts of dexlansoprazole.

8 Claims, 5 Drawing Sheets

SALTS OF DEXLANSOPRAZOLE AND THEIR PREPARATION

FIELD OF THE INVENTION

The present invention relates to the alkali metal, alkaline earth metal, ammonium or an amine salt of dexlansoprazole in amorphous form. The present invention further relates to processes for the preparation of these salts of dexlansoprazole.

BACKGROUND OF THE INVENTION

Dexlansoprazole is chemically described as 2-[(R)-{[3-methyl-4-(2,2,2-trifluoroethoxy)pyridin-2-yl]methyl}sulfinyl]-1H-benzimidazole as represented by Formula I.

FORMULA I

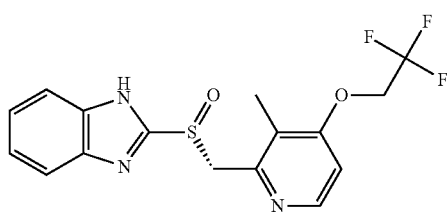

U.S. Pat. Nos. 6,462,058 and 7,285,668 and U.S. Publication No. 2007/0004779 describe processes for preparing crystalline forms of dexlansoprazole and its hydrates. PCT Publication No. WO 2009/117489 describes processes for the preparation of amorphous dexlansoprazole.

U.S. Pat. No. 7,271,182 discloses the formation of alkali and alkaline earth metal salts—such as sodium, magnesium, lithium, potassium, calcium, and barium—of dexlansoprazole, by reacting dexlansoprazole with a metal hydroxide, a metal alkoxide or a metal amide. It further says that the reaction is usually carried out in the presence of an inert solvent or in the absence of a solvent altogether. It provides water, alcohols, ketones, nitriles, amides, ethers, esters, halogenated hydrocarbons, hydrocarbons, sulfoxides, polar solvents, and the mixed solvents of two kinds or more, as examples of inert solvents. U.S. Pat. No. 7,271,182 describes specific methods for preparing crystals of sodium, potassium and magnesium salts of dexlansoprazole from dexlansoprazole, which involve multiple isolation steps and treatments with solvents such as methanol, ethanol, isopropanol, water, diethyl ether, toluene, and t-butyl methyl ether. These methods mention the use of foamy or amorphous material of the above salts at crude stage.

SUMMARY OF THE INVENTION

The present inventors have found that dexlansoprazole can be directly converted into the alkali metal, alkaline earth metal, ammonium or an amine salt of dexlansoprazole in amorphous form, in a single step process. The present process does not involve complex multi-step treatments with solvents. Thus, the present process is simple, economic and industrially preferable for preparing the preparation of high purity alkali metal, alkaline earth metal, ammonium or an amine salt of dexlansoprazole in amorphous form.

DETAILED DESCRIPTION OF THE INVENTION

Figure 1:
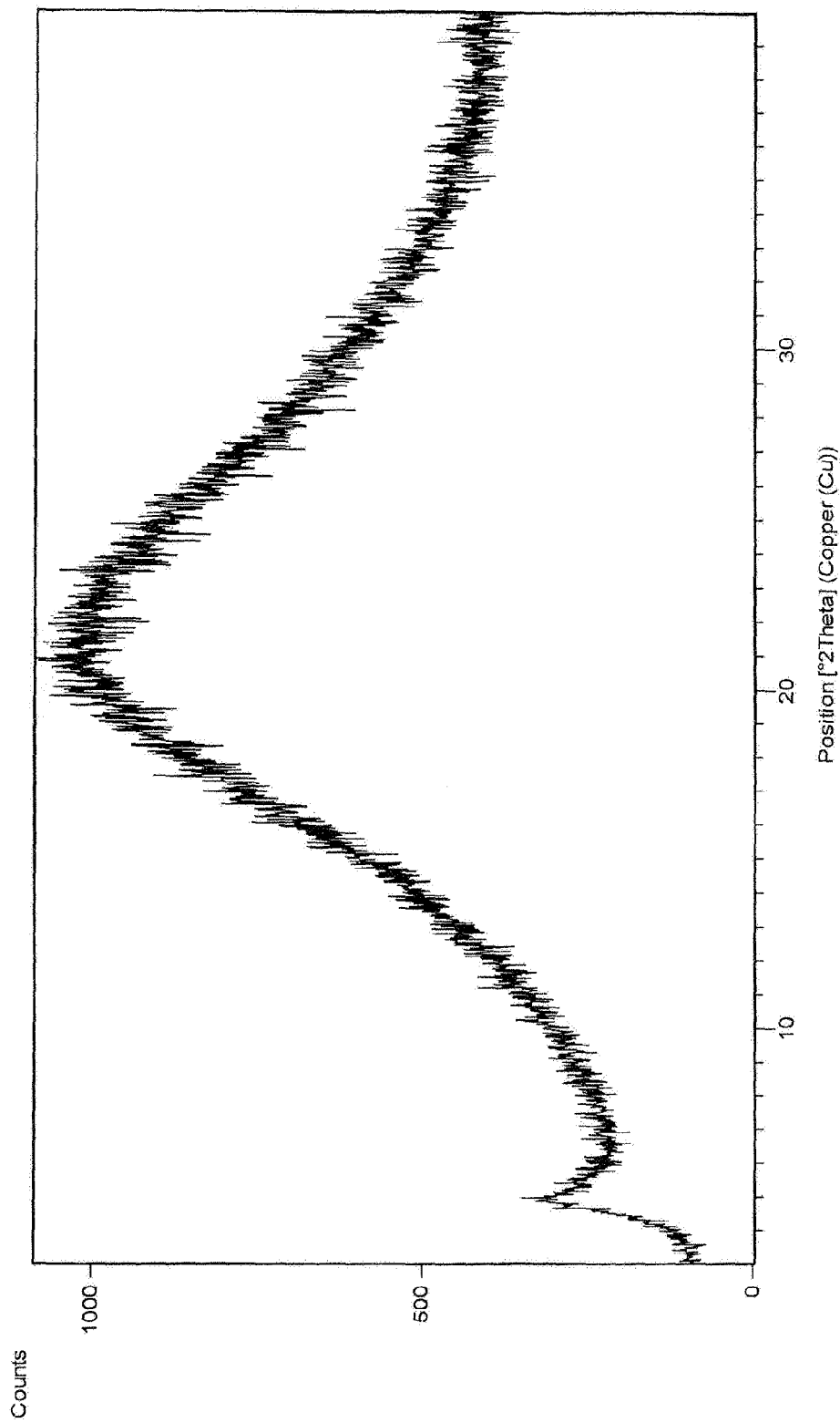
FIG. 1 depicts the X-ray powder diffraction pattern (XRPD) of the amorphous form of sodium salt of dexlansoprazole.
Figure 2:
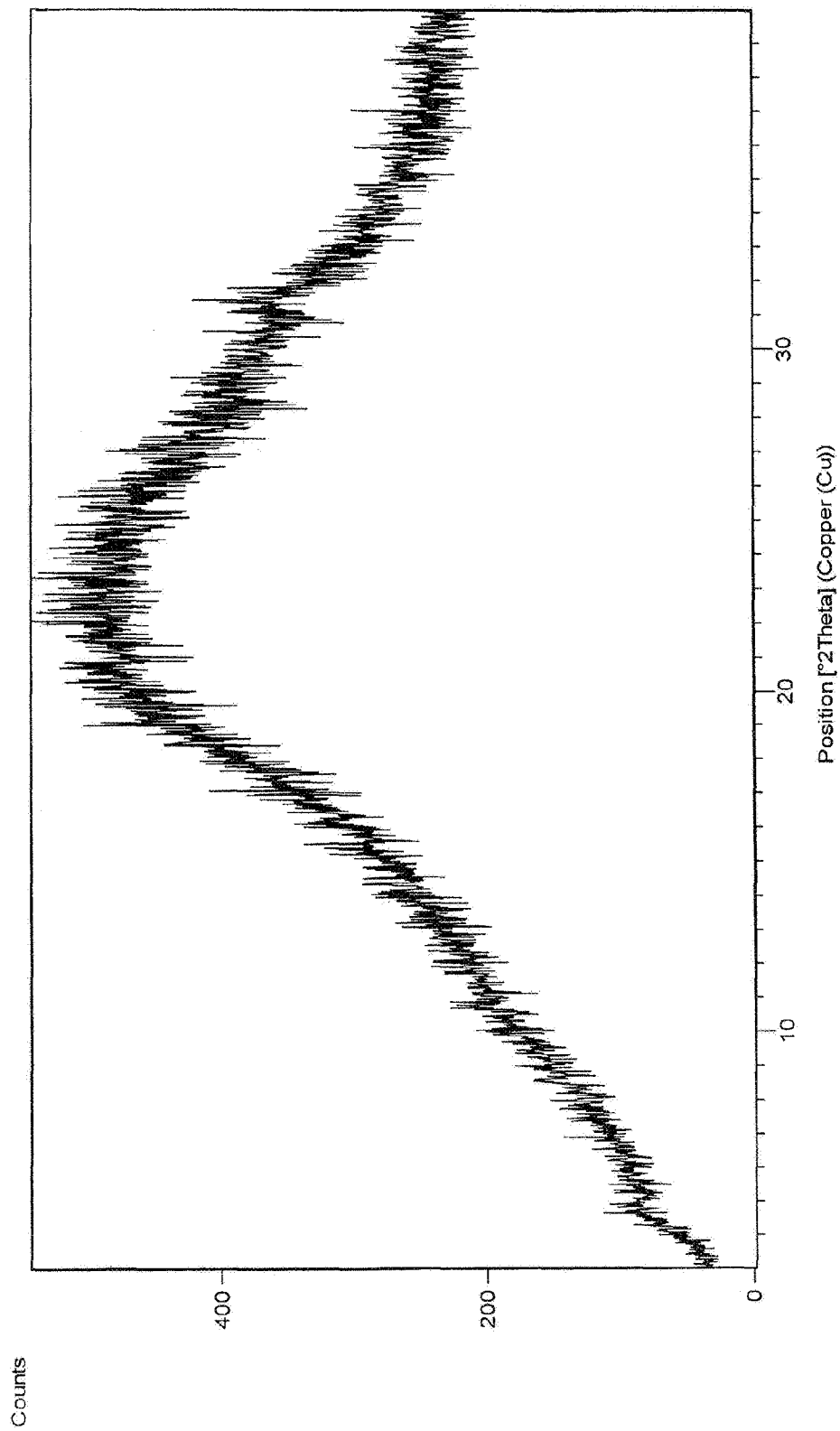
FIG. 2 depicts the X-ray powder diffraction pattern (XRPD) of the amorphous form of potassium salt of dexlansoprazole.
Figure 3:
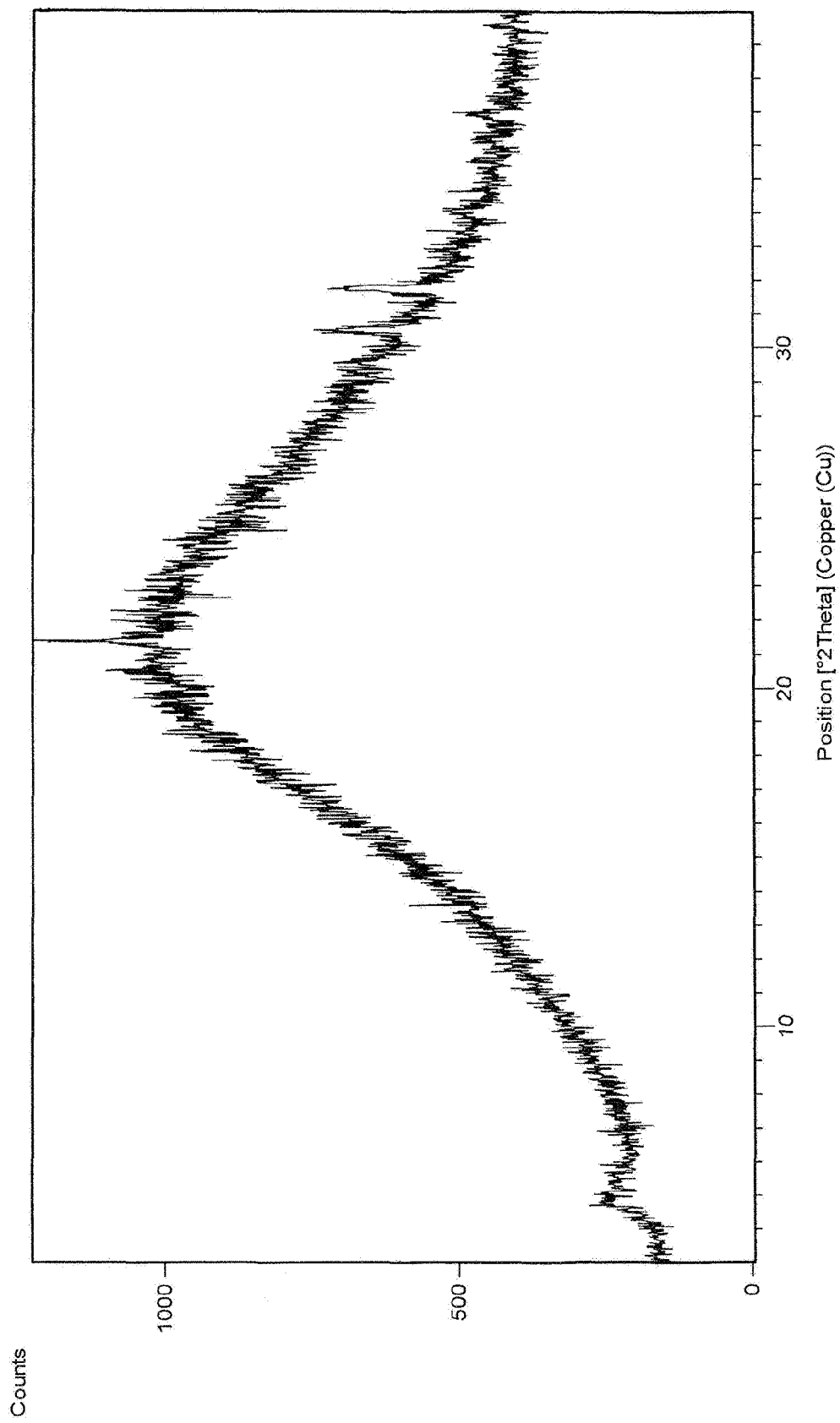
FIG. 3 depicts the X-ray powder diffraction pattern (XRPD) of the amorphous form of lithium salt of dexlansoprazole.
Figure 4:
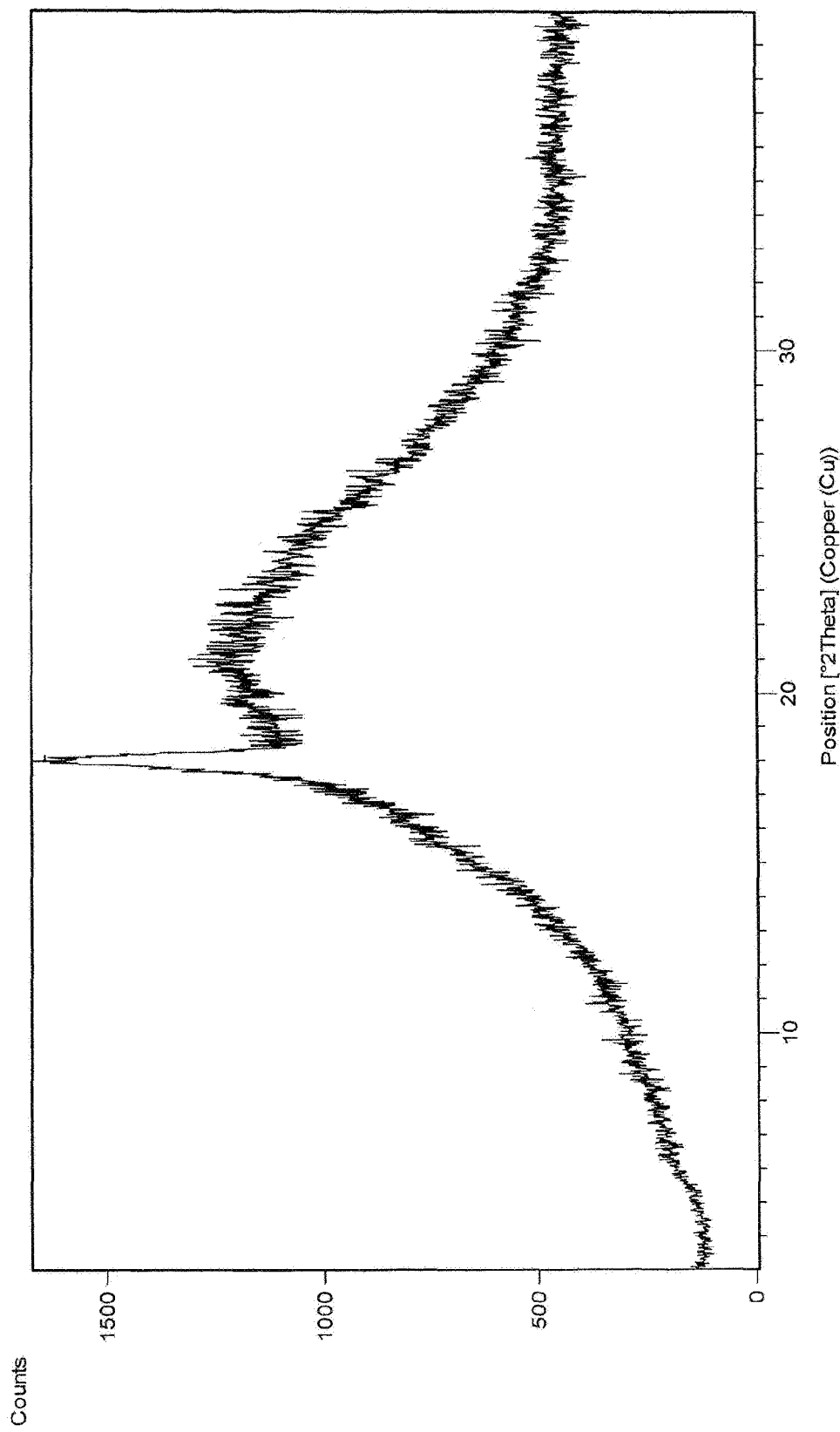
FIG. 4 depicts the X-ray powder diffraction pattern (XRPD) of the amorphous form of ammonium salt of dexlansoprazole.
Figure 5:
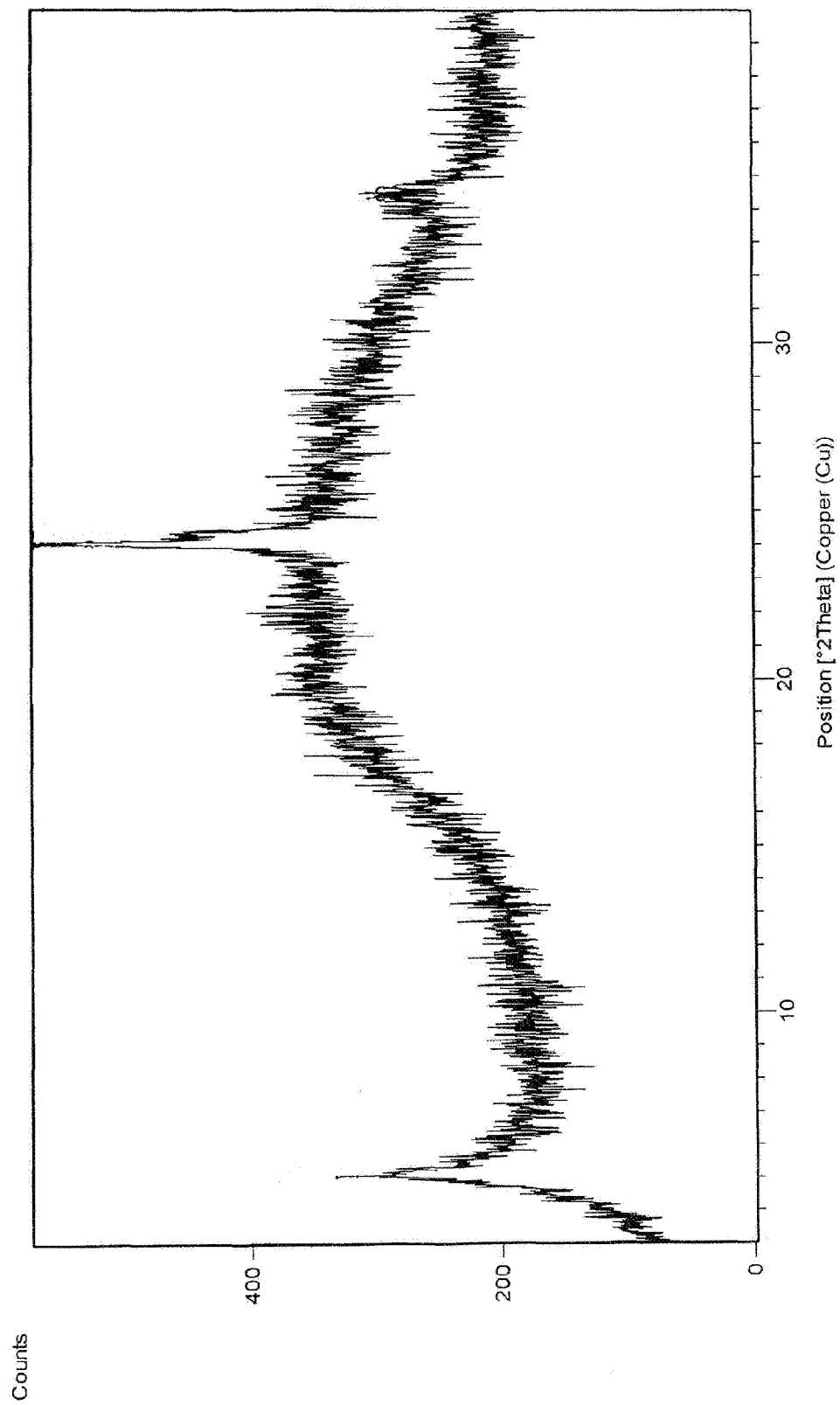
FIG. 5 depicts the X-ray powder diffraction pattern (XRPD) of the amorphous form of barium salt of dexlansoprazole.

A first aspect of the present invention provides a process for the preparation of alkali metal, alkaline earth metal, ammonium or an amine salt of dexlansoprazole in amorphous form, wherein the process comprises:
  a) contacting dexlansoprazole with a base selected from a group consisting of an alkali metal hydroxide, alkaline earth metal hydroxide, ammonia, and an amine in the presence of water; and
  b) isolating the alkali metal, alkaline earth metal, ammonium or an amine salt of dexlansoprazole in amorphous form the mixture.

The dexlansoprazole used as a starting material may be prepared according to the methods described in U.S. Pat. Nos. 6,462,058 and 7,285,668 and may be in any form. It may be in solid form, or in the form of a mixture with an organic solvent, which includes a solution, partial solution, semisolid, suspension and emulsion, obtained directly from the reaction mixture of preparing dexlansoprazole. The organic solvent may be an aliphatic or aromatic hydrocarbon, for example, toluene. The dexlansoprazole is contacted with a base selected from a group consisting of an alkali metal or alkaline earth metal hydroxide or an amine in the presence of water. The alkali metal hydroxide may be, for example, sodium, potassium or lithium hydroxide. The alkaline earth metal hydroxide may be, for example, magnesium, calcium, strontium or barium hydroxide. The amine may be a primary, secondary or tertiary amine, for example, n-propylamine, n-butylamine, t-butylamine, cyclohexylamine, cyclopentylamine, cycloheptylamine, cyclooctylamine, cyclododecylamine, benzylamine, and phenethylamine. Contacting dexlansoprazole with the base in the presence of water may be performed by mixing water, dexlansoprazole and the base in optional order of succession. For example, water may be mixed with dexlansoprazole prior to contacting with base, or water may be mixed with the base to obtain, for example, an aqueous solution of the base, prior to contacting with dexlansoprazole, or water may be mixed with dexlansoprazole after contacting with the base. A combination of above options may also be performed. The formation of the salt of dexlansoprazole with the base selected from a group consisting of an alkali metal hydroxide, alkaline earth metal hydroxide, ammonia, and an amine may be effected by stirring, heating, cooling, or a combination thereof. The alkali metal, alkaline earth metal, ammonium or an amine salt of dexlansoprazole in amorphous form may be isolated from the reaction mixture by filtration, decantation, evaporation, distillation, or a combination thereof.

A second aspect of the present invention provides an alkali metal, alkaline earth metal, ammonium or an amine salt of dexlansoprazole in amorphous form. The alkali metal, alkaline earth metal, ammonium or an amine salt of dexlansoprazole is preferably sodium salt of dexlansoprazole, potassium salt of dexlansoprazole, lithium salt of dexlansoprazole, ammonium salt of dexlansoprazole, strontium salt of dexlansoprazole or barium salt of dexlansoprazole. The sodium salt of dexlansoprazole, potassium salt of dexlansoprazole, lithium salt of dexlansoprazole, ammonium salt of dexlansoprazole and barium salt of dexlansoprazole have substantially the same XRPD patterns as depicted in FIGS. 1, 2, 3, 4 and 5, respectively.

Alkali metal, alkaline earth metal, ammonium or an amine salt of dexlansoprazole in amorphous form prepared by present invention may be further converted into dexlansoprazole which may be in crystalline form.

As used herein, the term "high purity" refers to chromatographic purity of not less than 99% and chiral purity of not less than 99%

XRPD of the samples were determined by using Panalytical X'Pert Pro X-Ray Powder Diffractometer in the range 3-40 degree 2 theta and under tube voltage and current of 45 Kv and 40 mA respectively. Copper radiation of wavelength 1.54 angstrom and Xceletor detector was used.

While the present invention has been described in terms of its specific embodiments, certain modifications and equivalents will be apparent to those skilled in the art and are intended to be included within the scope of the present invention.

EXAMPLES

Example 1

Preparation of Amorphous Form of Sodium Salt of Dexlansoprazole 2-({[3-Methyl-4-(2,2,2-trifluoroethoxy)pyridin-2-yl]methyl}sulfanyl)-1H-benzimidazole (900 g), L-diethyl tartarate (157.5 g), titanium isopropoxide (108.54 g) and toluene (9 L) were added together, heated to 45° C. to 50° C. and stirred for 1.5 hours at 45° C. to 50° C., followed by cooling to 20° C. to 25° C. Diisopropylethylamine (55.8 g) was added to the reaction mixture at 20° C. to 25° C. and stirred for 5 minutes to 10 minutes. Cumene hydroperoxide (508.32 g) was added drop-wise in 1.0 hours at 20° C. to 25° C. Aqueous sodium thiosulphate solution (450 g in 450 mL deionized water) was added in 10 minutes to 15 minutes at 20° C. to 25° C. The mixture was stirred for 5 minutes to 10 minutes and filtered through a Celite bed and washed with toluene (900 mL). The reaction mixture was allowed to settle followed by separation of the toluene layer. The toluene layer was added drop-wise into pre-heated (65° C. to 70° C.) aqueous sodium hydroxide solution (203.4 g sodium hydroxide in 7.2 L de-ionized water) in 0.5 hours. The mixture was stirred for 2 hours at 65° C. to 70° C., cooled to 20° C. to 25° C., stirred for 10 hours to 12 hours, filtered and washed with hot toluene (500 mL). The wet solid obtained was mixed with de-ionized water (4.5 L) and heated to 60° C. to 65° C. Toluene (4.5 L) was added to the mixture and stirred at 60° C. to 65° C. for 1 hour. The mixture was cooled to 30° C. to 35° C. and the solid was filtered. The wet solid obtained was washed with toluene (500 mL) at 30° C. to 35° C. De-ionized water (4.5 L) was added to the wet filtered solid and heated to 60° C. to 65° C. Toluene (4.5 L) was added to the mixture, stirred at 60° C. to 65° C. for 1 hour and cooled to 30° C. to 35° C. The wet solid was filtered and washed with toluene (500 mL) at 30° C. to 35° C. The solid was dried under vacuum at 50° C. to 55° C. for 10 hours to 12 hours to obtain the title compound as amorphous solid.

Yield: 51.8%
Chiral purity: 99.02%
Chromatographic purity: 98.58%
Moisture content: 1.87%

Example 2

Preparation of Amorphous Form of Lithium Salt of Dexlansoprazole 2-({[3-Methyl-4-(2,2,2-trifluoroethoxy)pyridin-2-yl]methyl}sulfanyl)-1H-benzimidazole (25 g), L-diethyl tartarate (3.6 g), titanium isopropoxide (2.6 g) and toluene (250 mL) were added together, heated to 45° C. to 50° C. and stirred for 1.5 hours at 45° C. to 50° C., followed by cooling to 20° C. to 25° C. Diisopropylethylamine (1.5 g) was added to the reaction mixture at 20° C. to 25° C. and stirred for 5 minutes to 10 minutes. Cumene hydroperoxide (14.12 g) was added drop-wise in 1.0 hour at 20° C. to 25° C. Aqueous sodium thiosulphate solution (25 g in 50 mL de-ionized water) was added in 10 minutes to 15 minutes at 20° C. to 25° C. The mixture was stirred for 5 minutes to 10 minutes and filtered through a Celite bed and washed with toluene (25 mL). The reaction mixture was allowed to settle followed by separation of the toluene layer. The toluene layer was divided into two equal parts. The first part of the toluene layer was added into aqueous lithium hydroxide solution (5 g lithium hydroxide in 125 mL de-ionized water) at 65° C. to 70° C. The mixture was cooled to 40° C. to 45° C. and stirred for 10 hours to 12 hours at 40° C. to 45° C. The mixture was filtered and washed with toluene (25 mL). The solid was dried under vacuum at 50° C. to 55° C. for 10 hours to 12 hours to obtain the title compound.

Yield: 75.5%
Moisture content: 2.99%

Example 3

Preparation of Amorphous Form of Potassium Salt of Dexlansoprazole

The second part of the toluene layer as obtained according to Example 2 was added into aqueous potassium hydroxide solution (4.5 g lithium hydroxide in 125 mL de-ionized water) at 65° C. to 70° C. The mixture was cooled to 40° C. to 45° C. and stirred for 10 hours to 12 hours at 40° C. to 45° C. The mixture was filtered and washed with toluene (25 mL). The solid was dried under vacuum at 50° C. to 55° C. for 10 hours to 12 hours to obtain the title compound.

Yield: 76.5%
Moisture content: 3.59%

Example 4

Preparation of Amorphous Form of Sodium Salt of Dexlansoprazole

A mixture of dexlansoprazole (3.0 g), de-ionized water (13.75 mL) and sodium hydroxide solution (649 mg in 16.25 mL of water) was heated to 60° C. to 65° C. and stirred for 2 hours at 60° C. to 65° C. The mixture was cooled to 16° C. and stirred for 2 hours. The mixture was filtered. The solid was dried under vacuum at 30° C. to 35° C. for 10 hours to 12 hours under calcium chloride to obtain the title compound.
Yield: 87.7%
Chiral purity: 99.7%
Chromatographic purity: 99.35%
Moisture content: 8.0%

Example 5

Preparation of Amorphous Form of Potassium Salt of Dexlansoprazole

A mixture of dexlansoprazole (3.0 g), de-ionized water (13.75 mL) and potassium hydroxide solution (910 mg in 16.25 mL of de-ionized water) was heated to 60° C. to 65° C. and stirred for 2 hours at 60° C. to 65° C. The mixture was cooled to 16° C. and stirred for 2 hours. The mixture was filtered. The solid was dried under vacuum at 30° C. to 35° C. for 10 hours to 12 hours under calcium chloride to obtain the title compound.
Yield: 87.8%
Chiral purity: 99.71%
Chromatographic purity: 99.39%
Moisture content: 8.7%

Example 6

Preparation of Amorphous Form of Lithium Salt of Dexlansoprazole

A mixture of dexlansoprazole (3.0 g), de-ionized water (13.75 mL) and lithium hydroxide solution (388 mg in 16.25 mL of de-ionized water) was heated to 60° C. to 65° C. and stirred for 2 hours at 65° C. to 70° C. The mixture was cooled to 16° C. and stirred for 2 hours. The mixture was filtered. The solid was dried under vacuum at 30° C. to 35° C. for 10 hours to 12 hours under calcium chloride to obtain the title compound.
Chiral purity: 99.71%
Chromatographic purity: 99.36%
Moisture content: 6.92%

Example 7

Preparation of Amorphous Form of Ammonium Salt of Dexlansoprazole

A mixture of dexlansoprazole (3.0 g), de-ionized water (28 mL) and aqueous ammonia solution (2 mL; 6%) was heated to 60° C. to 65° C. and stirred for 2 hours at 65° C. to 70° C. Aqueous ammonia solution (2 mL; 6%) was added to the mixture, heated to 60° C. to 65° C. and stirred for 0.5 hours at 65° C. to 70° C. The mixture was cooled to 16° C. and stirred for 10 hours to 12 hours. The mixture was filtered. The solid was dried under vacuum at 30° C. to 35° C. for 16 hours under calcium chloride to obtain the title compound.
Yield: 60.6%.
Chiral purity: 99.19%
Chromatographic purity: 98.36%
Moisture content: 2.77%

Example 8

Preparation of Amorphous Form of Barium Salt of Dexlansoprazole

A mixture of dexlansoprazole (4.0 g) and aqueous barium hydroxide solution (3.5 g of barium hydroxide octahydrate in 60 mL of de-ionized water) was heated to 65° C. to 70° C. and stirred for 1 hour at 65° C. to 70° C. The mixture was cooled to 26° C. with stirring for 1.5 hours. The mixture was filtered. The solid was dried under vacuum at 60° C. to 65° C. for 16 hours under calcium chloride to obtain the title compound.
Yield: 84.7%
Chiral purity: 99.64%
Moisture content: 6.61%

We claim:

1. A process for the preparation of the sodium salt of dexlansoprazole in amorphous form, wherein the process comprises:
   a) contacting dexlansoprazole with sodium hydroxide in the presence of water; and
   b) isolating the sodium salt of dexlansoprazole in amorphous form from the mixture thereof.

2. The process according to the claim 1, wherein the sodium salt of dexlansoprazole in amorphous form is further converted into crystalline dexlansoprazole.

3. Sodium salt of dexlansoprazole in amorphous form.

4. Sodium salt of dexlansoprazole in amorphous form according to claim 3 having substantially the same XRPD pattern as depicted in FIG. 1.

5. An amorphous sodium metal salt of dexlansoprazole according to claim 3, wherein the salt has high purity.

6. An amorphous sodium metal of claim 5 wherein the high purity is not less than 98.5% chromatographic purity.

7. An amorphous sodium metal of claim 5 wherein the high purity is not less than 99% chromatographic purity.

8. An amorphous sodium metal of claim 5 wherein the high purity is not less than 99% chiral purity.

* * * * *